United States Patent
Sluka et al.

[11] Patent Number: 5,932,296
[45] Date of Patent: Aug. 3, 1999

[54] PROCESS FOR PRODUCING A SURFACE COATED WITH AMINO GROUPS

[75] Inventors: Peter Sluka, Weilheim; Dierk Beyer, Mainz; Helmut Ringsdorf, Mainz-gonsenheim; Wolfgang Knoll, Mainz, all of Germany

[73] Assignee: Boehringer Mannheim GmbH, Mannheim, Germany

[21] Appl. No.: 08/852,412

[22] Filed: May 7, 1997

[30] Foreign Application Priority Data

May 10, 1996 [DE] Germany .................... 196 18 926

[51] Int. Cl.⁶ ....................................................... C08J 7/18

[52] U.S. Cl. ...................... 427/491; 427/301; 427/322; 427/402; 427/492; 427/536; 427/569; 428/411.1

[58] Field of Search .................... 427/491, 492, 427/536, 569, 322, 301, 402; 428/411.1

*Primary Examiner*—Bernard Pianalto
*Attorney, Agent, or Firm*—Nikaido, Marmelstein, Murray & Oram, LLP

[57] ABSTRACT

A surface coated with amino groups is produced by applying a polymerizable amine to a surface by means of a pulsed plasma. The coated surfaces obtained thereby have a high density of amino groups so that a specific binding phase can be obtained by covalently binding a partner of a specific binding pair to the surfaces coated with amino groups.

30 Claims, 2 Drawing Sheets

B-1

P-1

P-2

P-3

P-4

P-5

PROCESS FOR PRODUCING A SURFACE COATED WITH AMINO GROUPS

DESCRIPTION

The invention concerns a process for the production of a surface coated with amino groups and a surface with a high density of amino groups. In addition the invention concerns a process for the production of a specific binding phase using the surface coated with amino groups, a specific binding phase with improved properties and its use in immunoassays and in medical technology.

The interactions of proteins with polymer surfaces plays an important role in diagnostics. Polymer surfaces are for example used as solid phases for immunoassays or as implants in medical technology. In the case of immunoassays specific antibodies directed towards the analyte to be determined are usually bound adsorptively to the surface. However, the often very variable binding properties of proteins to surfaces which can result in a bleeding of the antibody or displacement reactions cause problems. These problems can to some extent be reduced by universal binding systems such as for example the streptavidin/biotin system.

A further problem in immunoassays is the occurrence of unspecific binding of other sample components to the surface such as serum or plasma proteins which leads to a reduction of the sensitivity and specificity of the detection method. Such unspecific interactions can result in a reduced binding of the analyte or to false-positive results. This problem of unspecific binding occurs in all detection methods in which other components that can adsorb to the surface are present in the sample in addition to the analyte. Examples of such samples are biological samples such as blood, blood components, serum etc.

In the past various methods have been described for modifying polymer surfaces with regard to a reduction in unspecific protein binding. In general it has been attempted to utilize the adsorption-reducing action of immobilized polyethylene glycols (PEG). N. Desai and J. Hubbell, J. Biomed. Mat. Res., Vol. 25 (1991), 829–843 describe a wet-chemical modification of polyethylene terephthalate surfaces by aminolysis and subsequent binding of cyanuric chloride-activated polyethylene glycols to the surface. However, a significant reduction of the protein binding as exemplified by fibrinogen was only seen at a polyethylene glycol molecular weight of at least 18,500. A further disadvantage is that the aminolysis process can hardly be controlled and is thus difficult to reproduce.

E. Kiss et al., Progr. Colloid & Polymer Sci., 74 (1987), 113–119 describe a modification of surfaces by grafting polyethylene glycol onto polyethylene in aqueous medium. For this polyethylene glycolaldehyde was coupled by means of reductive amination to amino groups of polyethylenimine which was adsorbed onto the polyethylene surface. This process is also difficult to reproduce and the modification of the surface is only statistical.

E. Uchida et al., Langmuir, 10 (1994), 481–485 describe a process for modifying polymer surfaces by applying acryl-derivatized polyethylene glycols by means of photo-induced grafting onto polyethylene terephthalate surfaces. WO92/07006 describes the modification of charged surfaces in an aqueous medium with polyethylene-coupled polyethylenimines. In this process the polymer is bound to the surface by pure ionic interactions so that the coated surface is sensitive to variations in the pH value.

Ratner et al., J. Biomed. Mat. Res. Vol. 26 (1992), 415–439 attempted to modify plastic surfaces by continuous wave (cw) plasma treatment in the presence of tetraethylene glycol dimethyl ethers. The production of these modified surfaces is difficult to reproduce and they have a low stability towards water which leads to a partial detachment of the layer. Since the layers are also very thin, further modification is almost impossible.

The modification of surfaces in the processes known in the state of the art is only achieved statistically and is poorly reproducible. The modification of surfaces in an aqueous environment as well as by treatment with continuous wave plasma (cw plasma) leads to a nonuniform statistical distribution of the amino groups on the surface. Therefore relatively long chain polyethylene glycol derivatives have to be immobilized in order to reduce unspecific bindings. The application of specific binding sites for analytes such as those that are necessary in order to use modified surfaces in immunoassays at the same time as PEG is almost impossible with these methods. In addition the previously known modified surfaces which have been coated by means of cw plasma require that subsequent chemical modifications are carried out using organic solvents. Polymers sensitive to solvents such as e.g. polystyrene which play an important role in diagnostics cannot be modified in this manner.

It was therefore an object of the invention to provide a process for the production of a surface coated with derivatizable amino groups with improved properties by means of which a specific binding phase can be obtained which has a high sensitivity and specificity.

The object is achieved according to the invention by a process for the production of a surface coated with amino groups wherein a polymerizable amine is applied to a surface by means of pulsed plasma.

The use of a pulsed plasma as described for example by V. Panchalingam et al., J. Biomater, Sci. polymer edition., vol. 5, No. ½(1993) 131–145, comprising a polymerizable amine surprisingly results in a surface which contains ca. 80% more nitrogen in the form of amino groups than surfaces produced by conventional means e.g. by conventional continuous wave plasma technology. The surfaces formed have a uniform amine coating and can be produced with good reproducibility.

The pulsed plasma is produced for example in a plasma reactor according to FIG. 1. Two electrodes (12) and (14) are installed in a container (10) that can be evacuated. The electrode (12) is connected to an apparatus for generating radio frequency pulses which is composed of a pulse generator (16), a radio frequency generator (18), a counter (20), a radio frequency amplifier (22), a watt meter (24), a bidirectional coupler (26), an oscilloscope (28) and a matching network (30). Radio frequency pulses are generated by the pulse generator (16) and radio frequency generator (18) and are amplified to the desired power by the radio frequency amplifier (22). The counter (20) as well as the watt meter (24) serve to observe the pulse durations, pulse frequencies as well as the pulse powers. The radio frequency pulses are passed to a bidirectional coupler (26). From this power is passed to an oscilloscope (28) which reflects the power of the bidirectional coupler (26). The radio frequency pulses are then applied to the electrode (12) via a matching network (30).

The surface (32) to be coated is placed between the electrodes (12) and (14) in the container (10) that can be evacuated.

The reactor is evacuated by a vacuum pump (34) and polymerizable amine is fed through an inlet (36). The pressure is monitored by a pressure measuring instrument (38). The device is additionally equipped with further inlet openings (40) through which further substances such as argon can be passed in. A pulsed plasma is produced by switching the power required for the plasma generation on and off by which means a plasma of the polymerizable amine is formed.

In order to achieve a uniform reproducible coating of the surface with a high amino group density, a pulsed plasma is used which has pulse durations of 0.5 to 1000 ms and a pulse frequency of 0.5 to 1000 Hz. Depending on the desired coating density the treatment period is between 1 minute and 2 hours. The pulsed plasma preferably has turn-on times of 1 to 100 ms and particularly preferably of 5 to 50 ms. The off-times are between 0.5 and 1000 ms preferably between 1 and 200 ms and particularly preferably between 5 and 100 ms. The power used to generate the plasma is preferably between 200 and 500 watts and particularly preferably between 50 and 300 watts. The suitable radio frequency depends on the reactor type and is about 13.56 MHz for the reactor shown in FIG. 1.

The polymerizable amine can be applied to the surface by means of the pulsed plasma in a single operating step. However, it is preferred to firstly clean the substrates by means of a pulsed argon plasma and subsequently to apply the polymerizable amine to the surface in two steps i.e. a priming step and a coating step. The priming is usually carried out with short off-times.

A primary or secondary amine can be used as the polymerizable amine which has a polymerizable group in addition to the amino group. The polymerizable group is preferably an unsaturated group such as a C=C double bond. The polymerizable amine or the applied vacuum must be selected such that the vapour pressure of the polymerizable amine is sufficient to ensure that at least a portion of the amine is in the gas phase under the applied vacuum conditions. Therefore readily volatile polymerizable amines with a high vapour pressure are preferably used. Examples of amines suitable for the invention are primary and secondary $C_2$–$C_8$ alkenyls and styrene derivatives which have a primary or secondary amino group. Allylamine is particularly preferably used as the polymerizable amine.

According to the invention the surface is composed of a plastic. In particular injection-mouldable plastics such as polycarbonate, polyethylene, polypropylene etc. are suitable. The surface is particularly preferably composed of polystyrene.

A further subject matter of the invention is a surface coated with amino groups obtainable by the process described above. Such a surface preferably has a density of the molecules containing the amino groups on the surface of at least 80% of the complete coverage particularly preferably of at least 95% of the complete coverage. In this case complete coverage is understood as the densest coating of the surface with a monomolecular layer of amine molecules that is theoretically possible with regard to the size of the molecule. The coating density can for example be determined by means of ESCA spectroscopy.

A surprising consequence of the high density and uniform distribution of the amino groups is that the surfaces according to the invention can be reproducibly modified. The modification is most suitably carried out by derivatization of the primary or secondary amino groups. As a result molecules with desirable functional groups or properties can be bound to the surface.

For example the reproducible high amine density on the surface achieved with the pulsed plasma enables the subsequent covalent binding of a partner of a specific binding pair to the surface coated with amino groups.

Hence a process for the production of a specific binding phase is a further subject matter of the invention. In this process a partner of a specific binding pair is covalently bound to a surface coated uniformly and with a high density with amino groups.

Specific binding pairs are known to a person skilled in the art and for example comprise the streptavidin-biotin system and also antibody-antigen or hapten pairs. Preferably biotin or a biotin analogue such as imino biotin or desthiobiotin is used. In this connection a biotin analogue is understood as any molecule capable of binding to streptavidin.

In this way the surface can be specifically furnished with specific binding sites which for example are capable of binding directly to an analyte or a specific binding partner. On the other hand the surface can also be coated with molecules such as polyethylene glycols which reduce unspecific binding of serum components to the surface in order to produce surfaces on which undesired adsorption or binding practically does not occur. Such surfaces can for example be used as implants in medical technology.

In addition to the partner of a specific binding pair, polyethylene glycol or a polyethylene glycol derivative is preferably bound to the surface coated with amino groups to obtain a specific binding phase in which unspecific interactions are further reduced. In this case the polyethylene glycol has an average chain length of 3 to 200 monomer units preferably of 3 to 50 monomer units and particularly preferably of 3 to 10 monomer units. The polyethylene glycol can be hydroxy- or alkyl-terminated.

Polyglycol and the partner of a specific binding pair are preferably used for binding to the surface in a molar ratio of 0:100 to 99:1, preferably in a molar ratio of 70:30 to 99:1 and especially preferably of 80:20 to 99:1. Surprisingly it was already possible to for example avoid the binding of fibrinogen by using short chain polyethylene glycol derivatives. The simultaneous incorporation of partners of a specific binding pair such as biotin and PEG enables the specific binding of e.g. streptavidin to the surfaces while at the same time minimizing the unspecific binding of other sample components such as e.g. fibrinogen.

A surprising result of the high density and uniform distribution of the amino groups on the surface is that the binding of the partner of a specific binding pair and optionally of the polyethylene glycol to the surface coated with amino groups can be carried out in aqueous solution. For example the partner of a specific binding pair and/or the polyethylene glycol can be used as an active ester derivative. In this case an active ester derivative is understood as a derivative of the partner of a specific binding pair or of polyethylene glycol which comprises an activated ester group which can react with an amino group in an aqueous medium. Examples of such active ester derivatives are shown in FIG. 2.

A further subject matter of the invention is a specific binding phase as can be obtained by one of the processes described above. Such a binding phase is characterized in that the partner of a specific binding pair and optionally polyethylene glycol is covalently linked to the amino groups applied to the surface. The surface is preferably coated with the applied amine by more than 80% and particularly preferably more than 95%.

A further subject matter of the invention is the use of such a specific binding phase as a solid phase in an immunoassay. In addition such a specific binding phase is also suitable for use in medical technology for example as an implant.

The invention is further elucidated by the attached Figures and examples.

EXAMPLE 1

Figure 1:
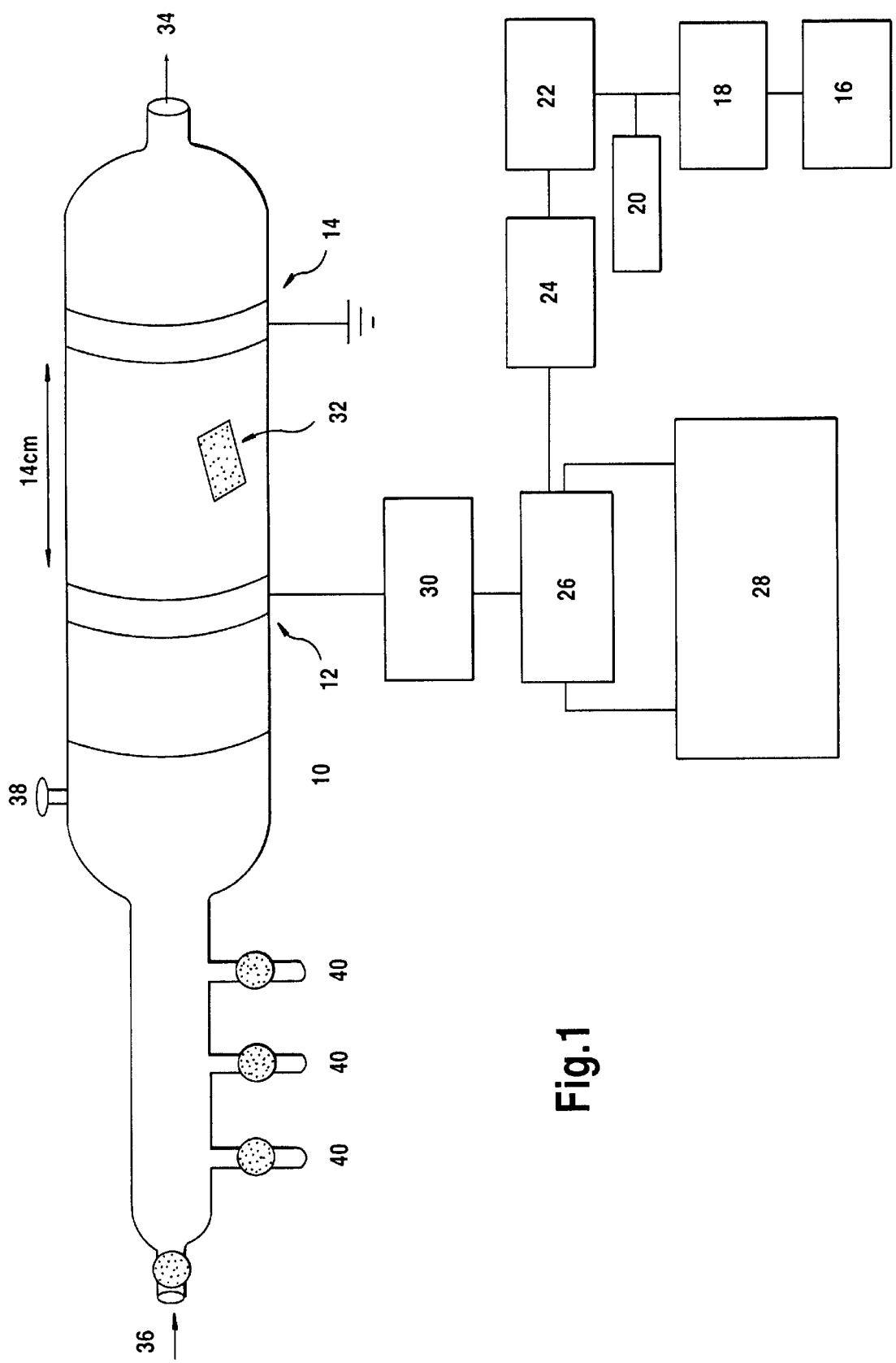
FIG. 1 shows a device for applying a polymerizable amine to a surface by means of a pulsed plasma and FIG. 2 shows preferred examples of active ester derivatives used according to the invention.

Production of a surface coating by grafting allylamine by means of a pulsed plasma In the device shown in FIG. 1 allylamine was deposited on a surface by means of a pulsed plasma. Injection-moulded polystyrene parts were used as substrates (2 cm ×1 cm×0.1 cm) which were previously cleaned in ethanol/water (1:2, v/v). The plasma coating was carried out in three steps under the following conditions:

1) Firstly the substrates were cleaned by means of an argon plasma. For this the polystyrene surfaces were subjected for 10 minutes to a pulsed argon plasma with turn-on times of 10 ms, off-times of 100 ms and a power of 100 watts.
2) After the cleaning an allylamine "priming" was applied to the polystyrene surface. This was carried out by means of a pulsed plasma with turn-on times of 3 ms, off-times of 5 ms and a power of 200 watts. The priming step was carried out for 4 minutes
3) Subsequently an allylamine surface layer was applied. The plasma conditions for this were 3 ms on-time 45 ms off-time and 200 watts power. The coating was carried out for 10 minutes.

EXAMPLE 2

Derivatization of the Surfaces Coated with Allylamine

Figure 2:
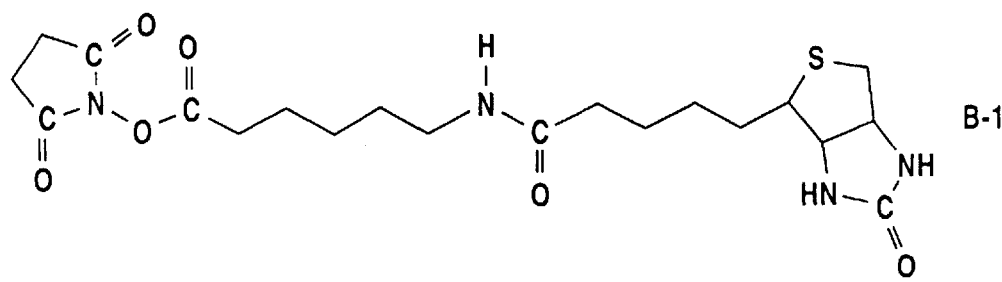
Figure 2:
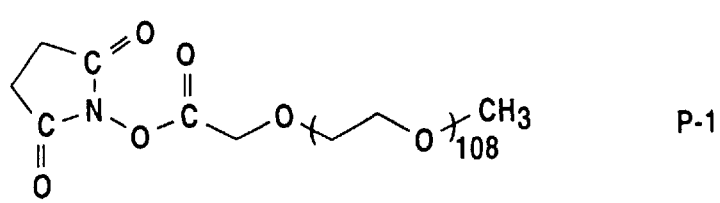
Figure 2:
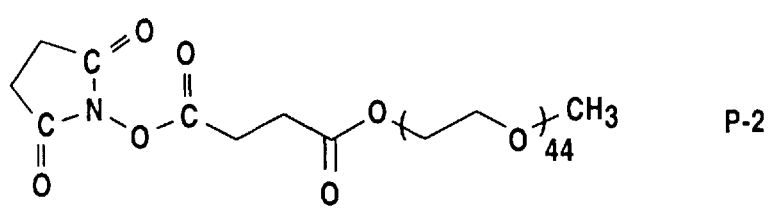
Figure 2:
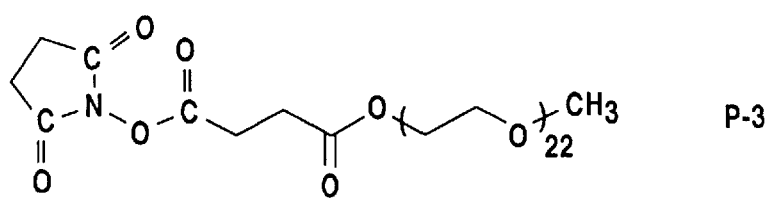
Figure 2:
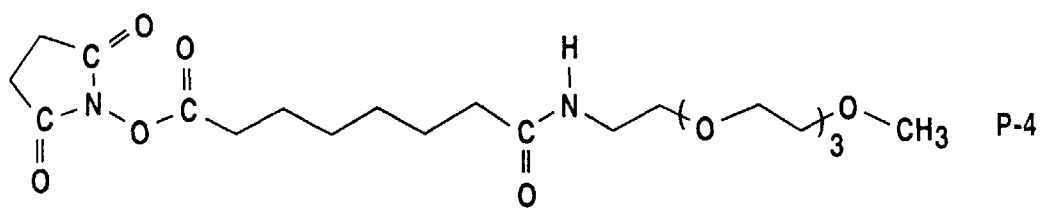
Figure 2:
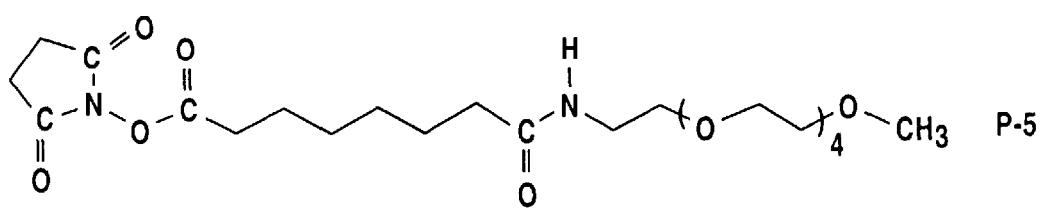

The allylamine-coated surfaces produced in the pulsed plasma were reacted with the compounds shown in FIG. 2 in an aqueous solution at pH 8. For this the surfaces coated with allylamine were reacted for 6 hours in a $10^{-3}$M aqueous solution buffered with phosphate buffer to pH=8 of the polyethylene glycols P1 to P5 present as active esters and of the active ester of biotin B1 in molar ratios of 0:1, 1:1, 7:3 and 9:1. The compound B1 was dissolved in a small amount of DMF before preparing the mixture and then added in the appropriate ratio to the aqueous solution of the polyethylene glycols P1 to P5.

EXAMPLE 3

Analytical Characterization of the Coated Surfaces by Means of Electron Spectroscopy for Chemical Applications (ESCA)

The elemental composition of surface layers can be determined quantitatively by means of ESCA spectroscopy. The surfaces coated with allylamine were examined before and after the chemical derivatization. When the freshly prepared surfaces coated with amino groups were stored under water there was a change in the surface composition which is due to the reaction of water with reactive species formed during the coating process. The quantitative analysis of the ESCA spectra with regard to the elemental composition for the various preparations is summarized in the following table:

TABLE 1

| Modification | | C1s [%] | O1s [%] | N1s [%] | S2p [%] |
|---|---|---|---|---|---|
| monomer (calculated) | | 75.0 | — | 25.0 | — |
| allylamine (cw) | | 77.7 | 6.8 | 15.6 | — |
| allylamine (cw) after buffer pH = 8 for 12 h | | 75.4 | 11.5 | 13.1 | |
| allylamine (pulsed) | | 71.0 | 5.2 | 23.8 | — |
| allylamine (pulsed) stored 12 h in buffer pH = 8 | | 70.8 | 10.8 | 18.4 | — |
| allylamine (pulsed) after reaction with B-1 in buffer | | 71.4 | 10.0 | 17.5 | 1.1 |
| P-2:B-1 | 1:1 | 65.9 | 21.3 | 12.1 | 0.65 |
| P-2:B-1 | 7:3 | 64.5 | 23.3 | 11.9 | 0.36 |
| P-2:B-1 | 9:1 | 66.7 | 24.9 | 8.1 | 0.22 |
| P-3:B-1 | 1:1 | 68.4 | 17.0 | 14.1 | 0.58 |
| P-3:B-1 | 7:3 | 66.8 | 22.9 | 9.9 | 0.35 |
| P-3:B-1 | 9:1 | 64.3 | 25.2 | 10.4 | 0.11 |
| P-4:B-1 | 1:1 | 72.5 | 11.4 | 15.5 | 0.62 |
| P-3:B1 | 7:3 | 72.8 | 12.3 | 14.5 | 0.39 |
| P-4:B-1 | 9:1 | 71.4 | 13.4 | 14.9 | 0.20 |
| P-5:B-1 | 1:1 | 71.3 | 11.4 | 16.6 | 0.68 |
| P-5:B-1 | 7:3 | 71.9 | 11.9 | 15.8 | 0.44 |
| P-5:B-1 | 9:1 | 71.5 | 13.1 | 15.3 | (0.10) |

It can be seen from table 1 that a coating density of 23.8 (N1s, pulsed plasma): 25.0 (N1s, monomolecular layer of allylamine) i.e. 95.2% of the complete coverage was achieved by means of the pulsed allylamine plasma.

EXAMPLE 4

Protein Adsorption to the Specific Binding Phases

The ability of the specific binding phases to bind streptavidin (specific binding) and fibrinogen (unspecific binding) was examined. A fluorescent labelled fibrinogen was used to detect the fibrinogen binding (bovine fibrinogen, FLUKA Company reacted with Resorufin-OSu, loading 1:1). The streptavidin binding was detected with fluorescent and biotinylated latex particles (Mol. -Probes Company L-5221, 100 nm, dye: yellow-green). The particle surface was biotinylated by covalent coupling with biotinylated bovine serum albumin (BSA).

a) Binding of Fibrinogen

The conjugate was dissolved in 100 mM potassium phosphate buffer pH 7.4 at a concentration of 1 mg/ml. This solution was incubated for 2 hours on the untreated surface as a control. The solution was applied to the specific binding phases, incubated for 2 hours and subsequently rinsed off with pure buffer solution. The specific binding phases were subsequently observed with a fluorescence microscope and the fluorescence of the surface was quantified by means of a CCD camera and image analysis (Optimetric, Stemer Co., Munich) as mean grey values of a defined image section.

b) Binding of Streptavidin

Streptavidin was dissolved in 100 mM potassium phosphate buffer, pH 7.4 at a concentration of 0.5 mg/ml. The specific binding phase was incubated for 2 hours with the solution and subsequently washed. The latex solution (0.5%) was then applied to the specific binding phase, it was incubated for 1 hour and subsequently washed. The fluorescence was observed and evaluated as in example 4a).

The results of the protein binding are summarized in table 2:

TABLE 2

| Surface | | Fibrinogen (mean grey) 515/650 nm | Streptavidin (mean grey) 450/500 nm |
|---|---|---|---|
| background/blank value | | 72 | 72 |
| polystyrene untreated | | 190 | 205 |
| P-1:B-1 | 7:3 | 87 | 162 |
| P-1:B-1 | 9:1 | 87 | 166 |
| P-2:B-1 | 7:3 | 88 | 139 |
| P-2:B-1 | 9:1 | 85 | 137 |
| P-4:B-1 | 7:3 | 86 | 190 |
| P-4:B-1 | 9:1 | 86 | 182 |

We claim:

1. A process for producing a surface coated with amino groups, comprising treating said surface with pulsed plasma in the presence of a polymerizable amine to attach said polymerizable amine thereto.

2. The process of claim 1, wherein said pulsed plasma has pulse durations of 0.5–1000 ms and a pulse frequency of 0.5–1000 Hz.

3. The process of claim 2, wherein said pulse plasmas has turn-on times of about 1–100 ms and off-times of about 1–200 ms.

4. The process of claim 3, wherein said pulsed plasma has turn-on times of about 5–50 ms and off-times of about 5–100 ms.

5. The process of claim 1, wherein said surface is treated with pulsed plasma for about 1 minute to about 2 hours.

6. The process of claim 1, further comprising generating said pulsed plasma with a power between about 20 and about 500 watts.

7. The process of claim 1, wherein said polymerizable amine is readily volatile.

8. The process of claim 7, wherein said polymerizable amine is $C_2$–$C_8$ alkene or styrene comprising a primary or secondary amino group.

9. The process of claim 8, wherein said polymerizable amine is allylamine.

10. The process of claim 1, wherein said surface is a surface of a plastic.

11. The process of claim 10, wherein said plastic is polystyrene.

12. The process of claim 1, wherein said surface is coated with amino groups at a density of at least 80% complete coverage.

13. The process of claim 12, wherein said surface is coated with amino groups at a density of at least 95% complete coverage.

14. The process of claim 1, further comprising cleaning said surface with a pulsed argon plasma before the treating step.

15. A process for producing a specific binding phase, comprising the following steps:
   (a) producing a surface coated with amino groups by the process of claim 1; and thereafter
   (b) covalently bonding a partner of a specific binding pair to said surface to form said specific binding phase.

16. The process of claim 15, wherein said partner is biotin or a biotin analogue.

17. The process of claim 16, wherein said biotin analogue is iminobiotin or desthiobiotin.

18. The process of claim 15, further comprising binding polyethylene glycol or a polyethylene glycol derivative to said surface.

19. The process of claim 18, wherein said polyethylene glycol has an average chain length of about 3–200 monomer units.

20. The process of claim 19, wherein said polyethylene glycol has an average chain length of about 3–50 monomer units.

21. The process of claim 19, wherein polyethylene glycol and said partner are bound to said surface at a molar ratio in the range of about 70:30 and about 99:1.

22. The process of claim 18, wherein polyethylene glycol and said partner are bound to said surface at a molar ratio in the range of about 0:100 and about 99:1.

23. The process of claim 18, further comprising binding polyethylene glycol or a derivative thereof to said surface in an aqueous solution.

24. The process of claim 18, wherein said partner or polyethylene glycol derivative comprises an activated ester group capable of reacting with an amino group in an aqueous medium.

25. In an immunoassay for an analyte, wherein a binding partner specific for said analyte is bound to a solid phase, an improvement comprising using as said solid phase a specific binding phase produced by the process of claim 18.

26. In a method of implanting a solid having a surface in a patient, an improvement comprising using as said surface a specific binding phase produced by the process of claim 18.

27. The process of claim 15, wherein said partner is covalently bonded to said amino groups in an aqueous solution.

28. In an immunoassay for an analyte, wherein a binding partner specific for said analyte is bound to a solid phase, an improvement comprising using as said solid phase a specific binding phase produced by the process of claim 15.

29. In a method of implanting a solid having a surface in a patient, an improvement comprising using as said surface a specific binding phase produced by the process of claim 15.

30. A process of producing a surface of polystyrene coated with amino groups, comprising the following steps
   (1) cleaning said surface using a pulsed argon plasma at a power of about 100 watts;
   (2) treating said surface with a pulsed plasma at a power of about 200 watts to form a "primed" surface;
   (3) placing allylamine on said "primed" surface; and thereafter
   (4) treating said "primed" surface with a pulsed plasma in the presence of allylamine at a power of about 200 watts to attach allylamine to said surface.

* * * * *